(12) United States Patent
Cotton

(10) Patent No.: US 12,277,272 B2
(45) Date of Patent: Apr. 15, 2025

(54) SYSTEMS AND METHODS FOR ELECTROMYOGRAM-BASED CONTROL USING NEURAL NETWORKS

(71) Applicant: REHABILITATION INSTITUTE OF CHICAGO, Chicago, IL (US)

(72) Inventor: Ronald James Cotton, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 17/769,394

(22) PCT Filed: Oct. 16, 2020

(86) PCT No.: PCT/US2020/056143
§ 371 (c)(1),
(2) Date: Apr. 15, 2022

(87) PCT Pub. No.: WO2021/077009
PCT Pub. Date: Apr. 22, 2021

(65) Prior Publication Data
US 2024/0184362 A1 Jun. 6, 2024

Related U.S. Application Data

(60) Provisional application No. 62/916,129, filed on Oct. 16, 2019.

(51) Int. Cl.
*G06F 3/01* (2006.01)
*A61F 4/00* (2006.01)
*G06N 3/084* (2023.01)
*G06N 3/09* (2023.01)

(52) U.S. Cl.
CPC ........... *G06F 3/015* (2013.01); *A61F 4/00* (2013.01); *G06N 3/084* (2013.01); *G06N 3/09* (2023.01)

(58) Field of Classification Search
CPC combination set(s) only.
See application file for complete search history.

(56) References Cited

U.S. PATENT DOCUMENTS

| 2005/0228515 A1 | 10/2005 | Musallam et al. |
| 2009/0005700 A1 * | 1/2009 | Joshi ............... A61B 5/389 600/546 |

(Continued)

FOREIGN PATENT DOCUMENTS

| EP | 3166033 A1 * | 5/2017 | ......... G06F 17/5009 |
| WO | 2018026842 A1 | 2/2018 | |

OTHER PUBLICATIONS

Ameri, A. et al., "Real-time, simultaneous myoelectric control using a convolutional neural network," PLOS One, Sep. 13, 2018, pp. 1-13.

(Continued)

*Primary Examiner* — Sanjiv D. Patel
(74) *Attorney, Agent, or Firm* — Polsinelli PC

(57) ABSTRACT

An EMG-based control system is disclosed. The system includes an EMG sensor that streams data to a device. A neural network executed by the device decodes muscle activity into a two-dimensional continuous control signal. A network-based calibration routine optimizes the neural network to decode natural movements of the user.

15 Claims, 16 Drawing Sheets

(56) References Cited

U.S. PATENT DOCUMENTS

| | | | | |
|---|---|---|---|---|
| 2009/0327171 | A1* | 12/2009 | Tan | G06F 3/015 |
| | | | | 706/12 |
| 2011/0224572 | A1* | 9/2011 | Gilja | G06F 3/015 |
| | | | | 600/545 |
| 2016/0140320 | A1* | 5/2016 | Moturu | G09B 7/06 |
| | | | | 434/236 |
| 2017/0220923 | A1* | 8/2017 | Bae | G06V 40/28 |
| 2017/0337682 | A1 | 11/2017 | Liao et al. | |
| 2019/0025917 | A1 | 1/2019 | Francis et al. | |
| 2019/0163270 | A1* | 5/2019 | Da Silva | A61B 5/486 |
| 2020/0107781 | A1* | 4/2020 | Navalgund | A61B 5/0004 |
| 2020/0282223 | A1* | 9/2020 | Schwemmer | G06N 3/045 |

OTHER PUBLICATIONS

Atzori, M. et al., "Deep Learning with Convolutional Neral Networks Applied to Electromyography Data: A Resource for the Classification of Movements for Prosthetic Hands," Frontiers in Neurorobotics, vol. 10, Article 9, Sep. 7, 2016, pp. 1-10.

Hargrove, L. J. et al., "Robotic Leg Control with EMG Decoding in an Amputee with Nerve Transfers," The New England Journal of Medicine, Sep. 26, 2013, pp. 1237-1242.

Patent Cooperation Treaty, International Search Report and Written Opinion, International Application No. PCT/US2020/056143, date of mailing Jan. 15, 2021, 15 pages.

* cited by examiner

SYSTEMS AND METHODS FOR ELECTROMYOGRAM-BASED CONTROL USING NEURAL NETWORKS

CROSS REFERENCE TO RELATED APPLICATIONS

This is a PCT application that claims benefit to U.S. provisional application Ser. No. 62/916,129 filed on Oct. 16, 2019 which is incorporated by reference in its entirety.

FIELD

The present disclosure generally relates to accessibility control for devices, and in particular, to an electromyography-based control system for mapping muscular electromyogram signals to a control scheme for various devices.

BACKGROUND

Spinal cord injury (SCI) affects approximately 18,000 people per year in the US and 250,000 to 500,000 people per year worldwide, with incomplete tetraplegia being the most common outcome. For people with higher-level cervical injuries, hand and arm impairments can particularly limit their ability to interact with the world and are consistently ranked highest amongst their rehabilitation priorities. Common adaptive solutions include controlling a smartphone with a mouth stick and a power wheelchair with a head array or sip-and-puff controller.

A number of methods have been proposed for two-dimensional control including brain-computer interfaces (BCI) with intracortical electrode arrays, electrocorticography and electroencephalography (EEG). While invasive approaches are promising, more research is required before these can be used routinely. EEG can be limited by signal noise, the difficulty of applying electrodes to the scalp, and the stability of the electrodes once placed. Activation from muscles with residual connections, which can extend below the neurological level of injury, can also be used. For example, inertial signals from the shoulders have been used to control a computer cursor or virtual keyboard or even a power wheelchair.

Muscle activation can also be acquired with electromyography (EMG). Substantial research has already been done towards restoring arm and hand function based on EMG, but the majority of this work targets the amputee population using signals from the residual limb. EMG from forearm extensors can allow people with SCI to control a cursor but many people with higher level cervical injuries often cannot activate these C7 innervated muscles. Some studies have demonstrated cursor control using a combination of head and neck EMG with head orientation. However, this approach struggled with diagonal movements and users might prefer retaining independent control of head movements when controlling a device. EMG from facial muscles has also been explored as a control source but similarly users might prefer not having electrodes on their face and retaining facial expressions for social interactions even when controlling a device.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
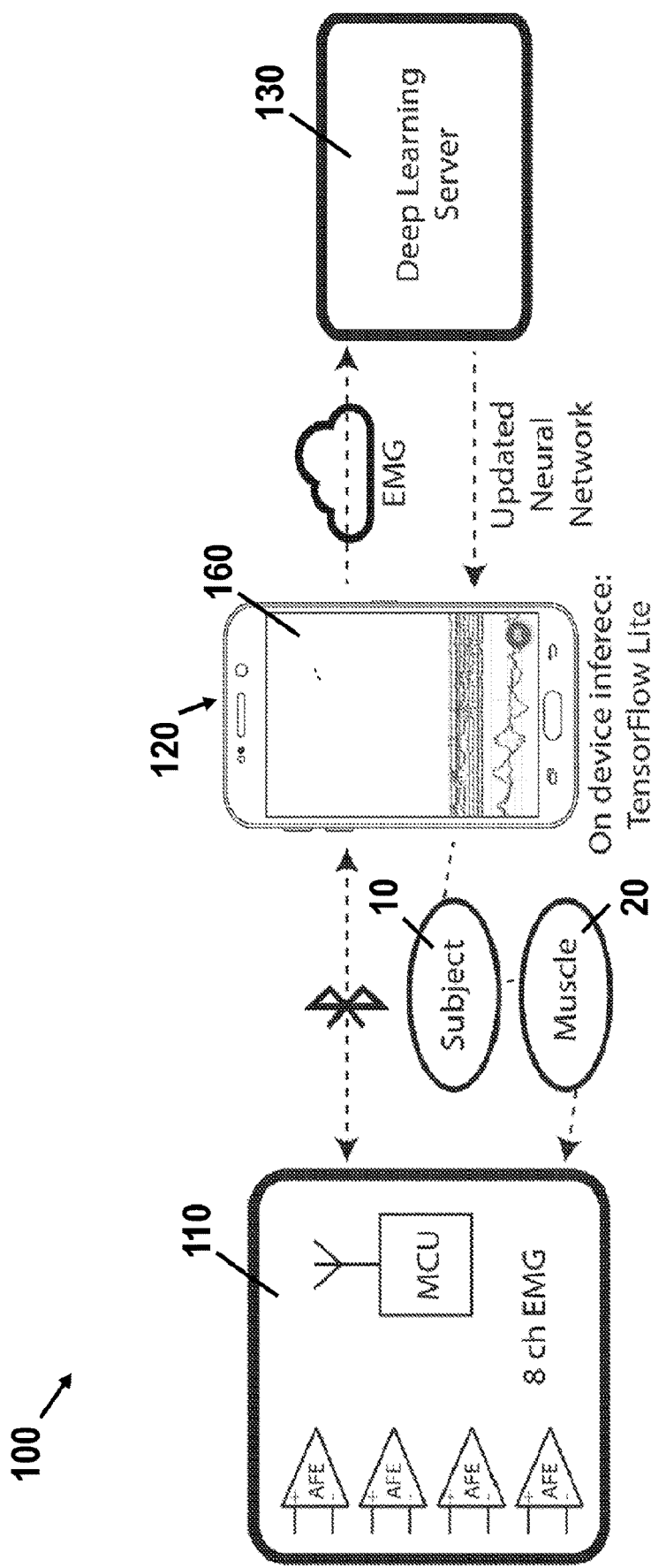
FIG. 1 is a diagram showing a system for EMG-based control of a device.

Various embodiments of a system and associated method for two-dimensional control of a device using wearable EMG are disclosed herein. In particular, the system includes a processor in communication with one or more EMG sensors configured to stream EMG data indicative of muscle activity to the processor. The system further includes an artificial neural network (ANN) in communication with or embodied by the processor to decode the EMG data indicative of muscle activity into a two-dimensional continuous control signal. The system further includes a neural network calibration routine to optimize the ANN to decode natural movements of the user to create a user-specific control scheme, rather than requiring the user to alter their behavior to the decoder. As discussed herein, the system is validated on participants with tetraplegia and the calibrated EMG decoder allows the participants to successfully control a cursor during a random target acquisition task. Finally, to test the system as a mobility controller, the participants used the present system to navigate in virtual reality. Referring to the drawings, embodiments of a system and associated method for control of a device using wearable EMG are illustrated and generally indicated as 100 in FIGS. 1-10.

Introduction

Driven largely by prosthetic control applications, methods for decoding EMG into intentions have expanded from direct control to include pattern recognition and more recently using artificial neural networks (ANN). Studies using ANNs to decode EMG have focused more frequently on discrete gesture recognition than on continuous control, often using signals from the forearm. Nonetheless, these results suggest that ANNs might be able to learn a flexible mapping from activity of cervically-innervated muscles to continuous cursor control. ANNs also tend to require significant amounts of training data so an important consideration is how long the system takes to calibrate, a design characteristic also important to end users. As a baseline, calibrating an intracortical brain-computer interface (BCI) using Kalman filters can be performed in 3 minutes.

Another design consideration is the physical design of the system. Historically, EMG decoding required wired connections to lab equipment analyzed by desktop computers, but technological advances have driven progress towards wireless and wearable systems with more onboard computing.

Decoders using ANNs still typically require a computer both to optimize the network parameters and run the networks inference. However, the increasing interest in edge-computing with ANNs has led to frameworks such as TensorFlow Lite that allow running them on smartphones.

A reliable, continuous, two-dimensional control signal as produced by the system 100 has applications beyond controlling a smartphone. Many people with high-level cervical SCI cannot operate the joystick control on a power wheelchair and use alternative methods such as a head-array or sip-and-puff. Other signals that have been explored include inertial, tongue drive, smarter wheelchairs and EMG. Having a consistent interface for a smartphone and for mobility could make controlling both easier. In addition, the ability to use BCI to control multiple devices is another design characteristic considered important by end users.

System Overview

Figure 2:
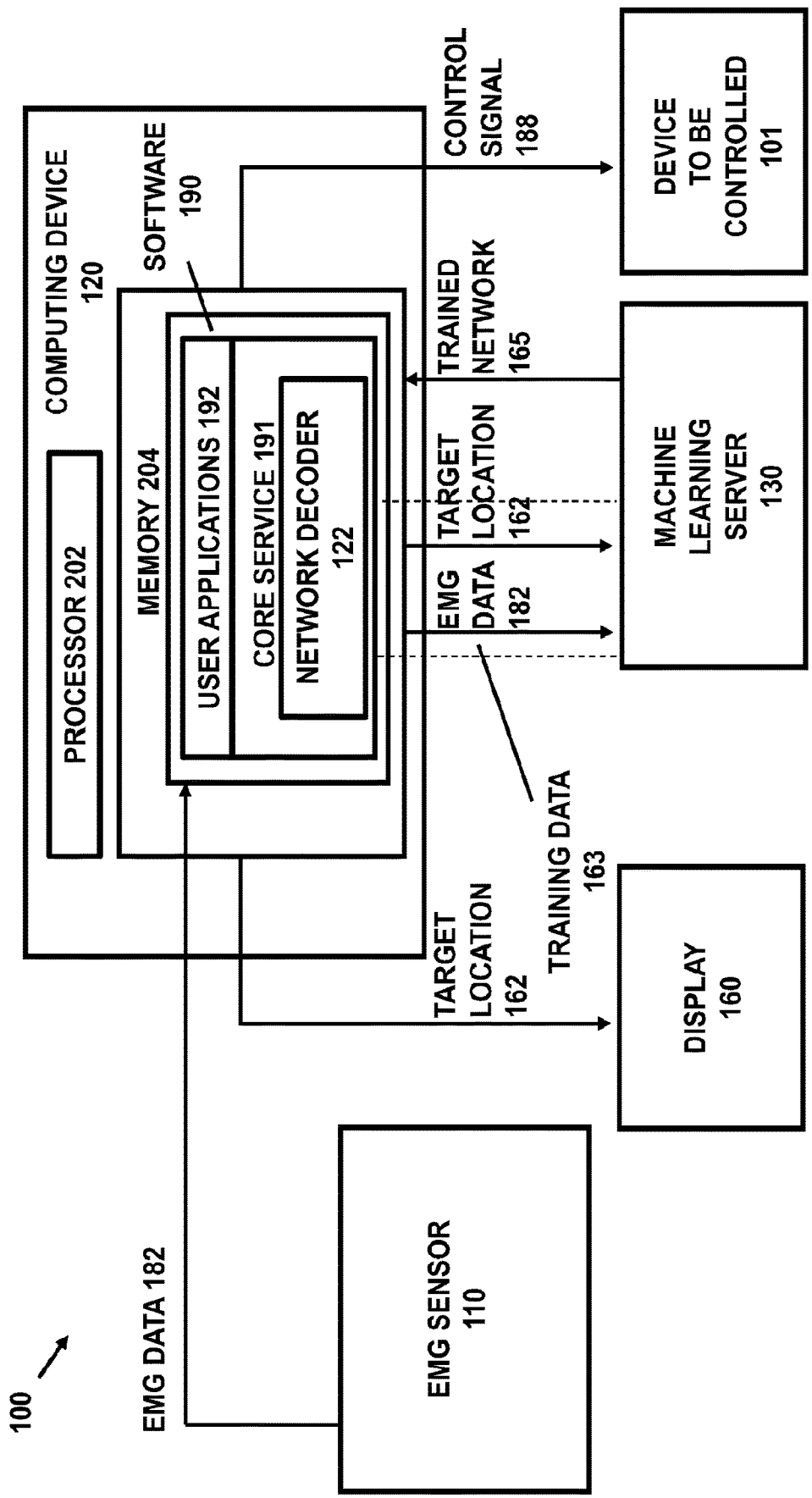
FIG. 2 is a diagram showing data flow between components of the system of FIG. 1.

Referring to FIGS. 1 and 2, the system 100 for continuous control of a device 101 includes a wearable EMG sensor 110 that acquires EMG data 182 from a muscle 20 of a user 10 communicates with a computing device 120. The computing device 120 decodes EMG data 182 acquired by the EMG sensor 110 and maps the EMG data 182 to a control scheme which can be used to operate the device 101 such as a smartphone, mobility chair, or other devices. In some embodiments, such as the case where the device 101 is a smartphone or computer, the device 101 to be controlled is also the computing device 120 itself. The EMG data 182 including a plurality of EMG samples is decoded into control signals 188 by a decoder 122 established onboard the computing device 120. In some embodiments, the computing device 120 communicates with a machine learning server 130 that optimizes the decoder 122 to recognize movements that are personal and fit to the user 10, allowing for intuitive control of devices. In one method of calibrating and using the system 100 to translate EMG data 182 into control signals 188 EMG activity is acquired by the sensor 110 from the muscle 20 of the user 10 and wirelessly transmitted to a computing device 120 where an on-device decoder 122 converts the EMG data 182 into a control signal 188 in real-time for control of the device 101. During optimization of the decoder 122, the user 10 performs a set of self-selected movements to mirror the location of a target 161 shown on a display 160. The EMG data 182 received by the computing device 120 is sent to the machine learning server 130, which optimizes parameters of the decoder 122 and transmits a trained decoder 165 back to the computing device 120.

In one embodiment of the system 100, the decoder 122 is a neural network running on the computing device 120 that decodes EMG data 182 into control signals 188. In some embodiments, the control signals 188 are a 2D continuous cursor 164 (FIG. 5) and in other embodiments could be extended to 2D with additional binary signals or even higher dimensions. The decoder 122 runs on the computing device 120 using a suitable machine-learning library such as TensorFlow Lite, which allows deploying pre-trained neural networks to mobile devices and other lightweight computing systems.

While neural networks are powerful function approximators, they must be trained to do anything useful. Currently, most smartphones are not powerful enough to quickly run optimization for more complicated neural networks. To avoid this problem, as shown in FIG. 2, training data 163 is streamed to the machine learning server 130, which optimizes parameters of the decoder 122 (i.e. trains the network) and transmits the trained decoder 165 back to the computing device 120, which continues to run in real time but with the updated model. As shown, the training data 163 includes EMG data 182 collected during a calibration routine and associated target locations 162 of a target 161 which appears on a display 160 during the calibration routine.

To train the system 100, the calibration target 161 is shown on the display 160 of the computing device 120. The user 10 makes self-selected movements to mirror the calibration target 161. Each target 161 has an associated target location 162, each target location 162 being a set of coordinates or another representation of the location of the target 161. In most embodiments, the target locations 162 are stored in the memory 204 as a pre-determined routine. A combination of target locations 162 (y) and recent EMG data 182 (X) are collected and sent to the machine learning server 130 to optimize parameters of the decoder 122. In some embodiments, each sample of EMG data 182 collected during the calibration routine has a dimension of 250×8, and each target location 162 has a dimension of 2. The machine learning server 130 uses supervised learning with back-propagation to train a function $f$ to map from X to y by optimizing the parameters of the network θ. Function $f$ interprets the users natural and self-selected movements to create a mapping between the user's intentions and the target locations 162.

$$f_\theta: \mathbb{R}^{250\times8} \to \mathbb{R}^2$$

$$y_t = f_\theta(X_t)$$

With $X_t$ being a recent history of EMG data 182 as obtained by the EMG sensor 110, $$X_t = \{x_i : i \in \{t, t-1, \ldots, t-T+1\}\}$$

The size of this will be determined by the sampling rate and amount of recent history used by the decoder—in this case 250 samples from 0.5 s with a sampling rate of 500 Hz. The set of $\{X_t, y_t\}$ is used as training data 163 for supervised learning on the neural network. In the current implementation, $f_\theta$ is a neural network consisting of several convolution layers operating on each channel to produce the EMG data 182 (i.e. amount of activity corresponding to muscle activity) for each channel. These activity measures for each channel over the recent history and then passed through an additional convolutional layer that allows mixing between the layers. Finally several densely connected layers are applied before outputting to the final control signals. In this case, these are two channels (horizontal and vertical) with a sigmoid non-linearity.

The trained decoder 122 is then used to control a device using EMG data 182 acquired by the EMG sensor 110, such as the velocity of a cursor 164 (FIG. 5) on a smartphone or computer (i.e. $\dot{P}_t = f_\theta(\bullet)$) or to drive a power wheelchair.

Network Design and Optimization

Figure 3:
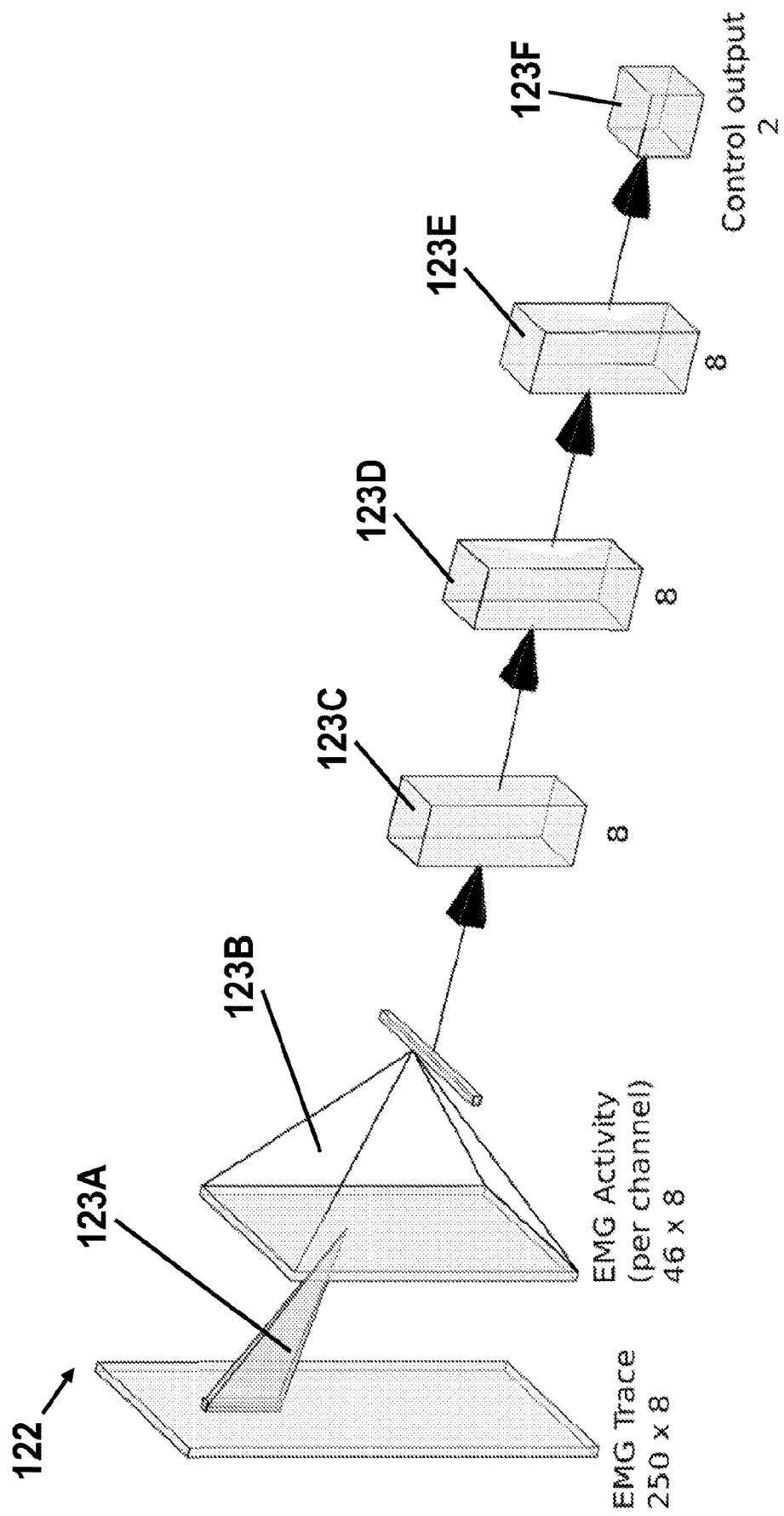
FIG. 3 is a diagram showing an architecture of a decoder of the system of FIG. 1.

Decoder Architecture: Referring to FIG. 3, in some embodiments the decoder 122 is implemented on the computing device 120 as a convolutional neural network using a neural network library such as TensorFlow Lite and using data collected during the optimization task. The decoder 122 maps the most recent 500 ms of EMG data 182 (250 samples at 500 Hz) from 8 channels into two continuous control signals 188 as shown:

$$f_\theta: \mathbb{R}^{250 \times 8} \to \mathbb{R}^2$$

The decoder 122 includes an initial set of fixed (i.e. not trainable) layers 123A to compute the root-mean power in EMG bandwidth for each channel. To make this compatible with a convolutional network, the root-mean power determination within a particular bandwidth was implemented as a convolution in the decoder 122 with minimum-phase coefficients using a 20th order FIR bandpass filter from 30-125 Hz, followed by a squared nonlinearity, followed by another convolution with a stride of 5 and minimum-phase coefficients from a 10 Hz lowpass FIR filter, followed by a square root non-linearity. The output of the initial set of fixed layers 123A was $\mathbb{R}^{46 \times 8}$, representing the EMG power from each channel in the last 500 ms.

The remaining layers all had learnable weights and biases. The most critical was a convolutional layer 123B, which captures the spatio-temporal patterns amongst the channels over the last 500 ms and outputs 8 features. By design, these features did not correspond in an explicit way to the underlying channels, rather, they were learned combinations of activity across the history and all 8 channels. These features were passed through three densely connected layers 123C, 123D and 123E, each with 8 hidden units and a ReLU non-linearity followed by a final densely connected layer 123F with two output channels. These outputs were passed through a sigmoid non-linearity to bound them from (0,1) to return control signals 188. This network architecture was flexible enough to perform well, but small enough to converge with a modest amount of data as described below. However, the approach was fairly robust to changes in model architecture based on refitting previously collected data.

2) Model Fitting: The decoder, $f_\theta$, was trained to map natural movements of an individual user to control signals by finding parameters, $\theta$ that minimized the loss, $\mathcal{L}(\theta)$, on training data 163 collected during the calibration procedure described below.

This training data 163 included simultaneously collected EMG data 182 and target locations 162 of the target 161. The training data 163 was downsampled to 10 Hz where samples contained the target location 162 at that time point, y, and the prior 500 ms of the 8-channel EMG data 182, x. The loss function $\mathcal{L}(\theta)$ is the Euclidean distance between the target location 162 and control signals 188 summed over the training data 163:

$$\mathcal{L}(\theta) = \sum_i \|y_i - f_\theta(X_i)\|$$

The loss was minimized by gradient descent using an Adam optimizer with a step size of $1 \times 10^{-4}$ a and with a minibatch size of 10. The loss also included an L2 weight decay of 0.01.

In some embodiments of the system 100, optimization occurs in parallel with the calibration routine. Because the user produces more training data as calibration continues, the training data 163 is continually updated to include the newly-acquired EMG data 182 at the end of each epoch. In some embodiments, the training data 163 is sampled in a biased manner, with more recent or new data sampled with higher probability or otherwise given higher weight than earlier or older data. This prevents earlier EMG data 182 from being overrepresented in the loss over the entire training procedure, and also encourages the decoder 122 to capture any changes in the user's behavior as they became more comfortable with the calibration routine. In one particular embodiment, the server 130 performing the optimization had an Nvidia 1080Ti GPU and the loss would typically plateau after 2-3 minutes. Every 2500 updates (approximately 10 seconds), the optimized decoder 122 is compiled to the machine learning library, serialized, and transmitted to the computing device 120 over a wireless or wired connection. On the computing device 120, the optimized decoder 122 is de-serialized and the computing device 120 begins using the updated decoder 122.

Continual Learning

In some embodiments, the decoder 122 is continually refined using inverse reinforcement learning, which attempts to model natural behavior of the user 10. Using this training signal, it is possible to continue to iteratively improve both a behavioral policy model and the model of the decoder 122 with a similar loss $\mathcal{L}(\theta)$ that replaces the known calibration target location 161 with the behavioral model. Practically speaking, in some embodiments both the behavioral policy and decoder 122 are jointly optimized together.

The process can be modeled where the user observes a game state $S_t = \{P_t, g_t\}$, with $p_t$ the current cursor location and $g_t$ a goal location, where the output of the decoder controls the velocity of the cursor and the user is attempted to move the cursor to the goal location. The user, based on their policy $\pi^-$ makes an action $a_t$, which results in recorded muscle activity $x_t$. So the system from the users observations to the change in the cursor can be written as:

$$\dot{p}_t = f_\theta(X_t)$$

$$s_t = \{p_t, g_t\}$$

$$a_t \sim \pi(s_t)$$

$$s_t \xrightarrow{\pi} a_t \xrightarrow{G} x_t \xrightarrow{f_\theta} \dot{p}_t$$

However, the underlying action $a_t$ is not directly observable, nor do we know the users internal policy. Thus we approximate these together as $\pi_\phi$:

$$s_t \xrightarrow{\pi?} a_t \xrightarrow{G} x_t \xrightarrow{f_\theta} \dot{p}_t$$

$$s_t \xrightarrow{\pi_\phi} \dot{p}_t$$

And then substitute the prediction of the behavior based on what the user is observing into the loss function to jointly optimize this behavioral policy and the decoder 122:

$$\mathcal{L} = \sum [f_\theta(X_t) - \pi_\phi(\{s_t, \ldots, s_0\})]^2$$

$$\mathcal{L} = \sum_t [f_\theta(X_t) - \pi_\phi(\{s_t, \ldots, s_0\})]^2 + C(\pi_\phi)$$

It is also important to encourage this joint optimization to find a combination of behavioral policy and EMG decoder 122 that are also consistent with solving the task. This requires a 'critic' of the behavioral policy that scores it based on how it performs on the task. In the approach used here, this critic measures how close the policy is to the optimal one (which involves going at full speed towards the target 161). However, this could be broadened and a stochastic could be evaluated based on other metrics such as the expected reward in the task.

This embodiment describes a task where the goal of the user 10 is known, such as that described below. In other embodiments when a user 10 is selecting an outcome from multiple possible goals, the decoder 122 can also include a technique that learns a policy that also infers the goal of the user 10, such as Hindsight Experience Replay.

Types of inverse reinforcement learning: Under this formulation with $\pi_\phi$ as a flexible network itself, this is an example of behavioral cloning. Behavioral cloning is a specific type of inverse reinforcement learning where the policy tries to predict the observed behaviors. However, there is another class of inverse reinforcement learning called Imitation Learning (and a related approach Inverse Rational Control) that attempts to more find the cost function (or rewards) for the task that would give rise to the observed behavior. By making the parameters that describe the policy, $\phi$, parameterize a cost function for the task and with $\pi_\phi$ the optimal policy under that cost function, then the same loss function described above can be jointly optimized. Imitation Learning can be more robust to particularly poor performance on the task than Behavioral Cloning, but requires pre-computing the mapping from $\phi$ to $\pi_\phi$ using a traditional reinforcement learning paradigm.

Hardware

Figure 4A:
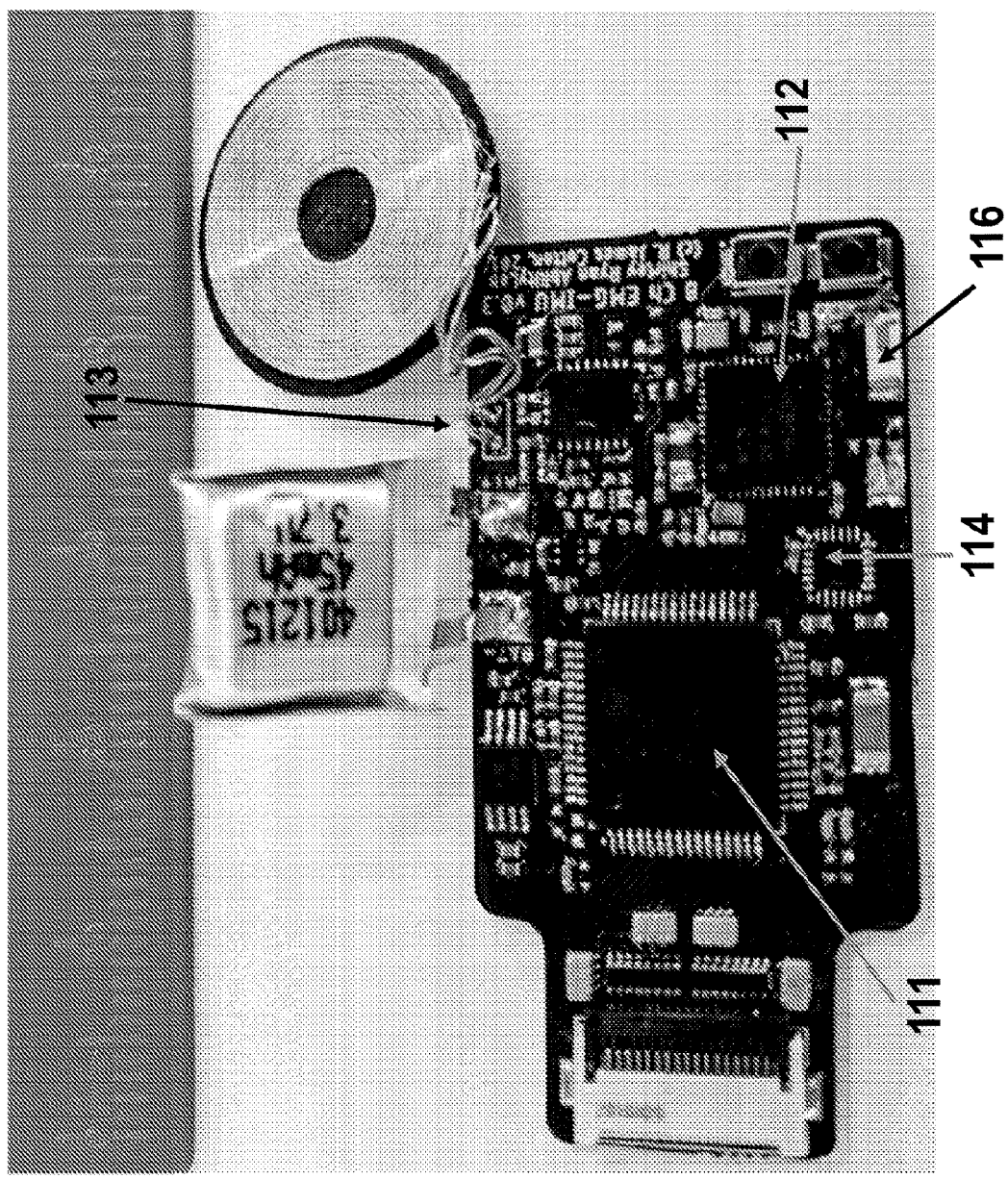
FIG. 4A is a photograph showing an EMG sensor of the system of FIG. 1.
Figure 4B:
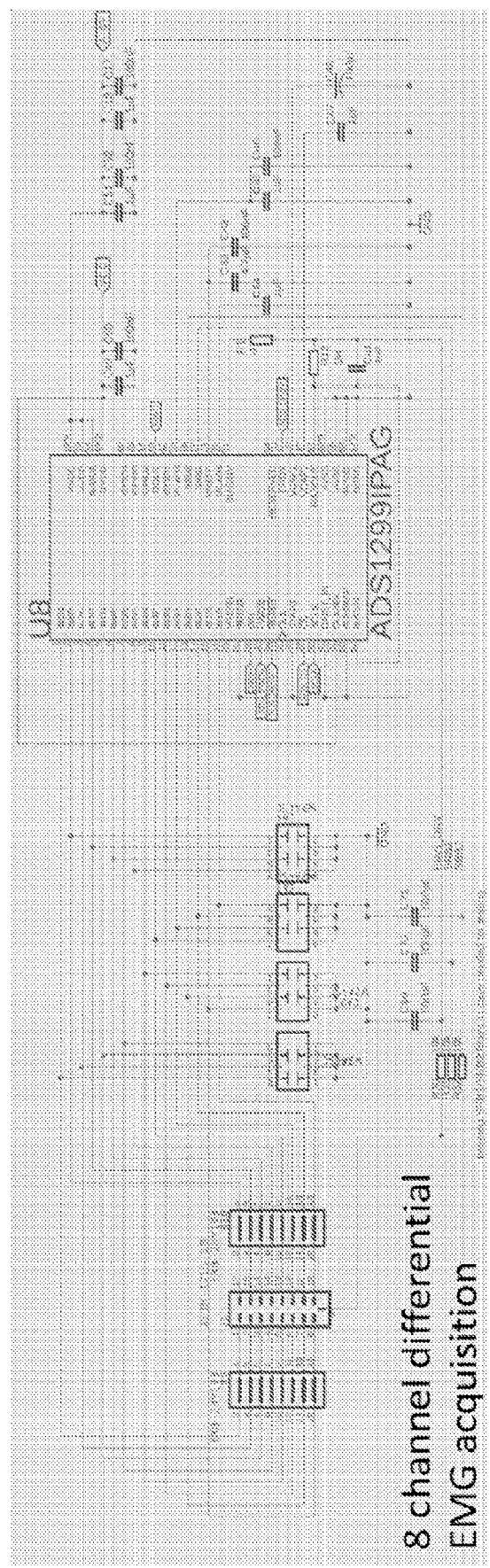
FIGS. 4B-4E are an electrical schematics representative of components of the EMG sensor of FIG. 4A.
Figure 4C:
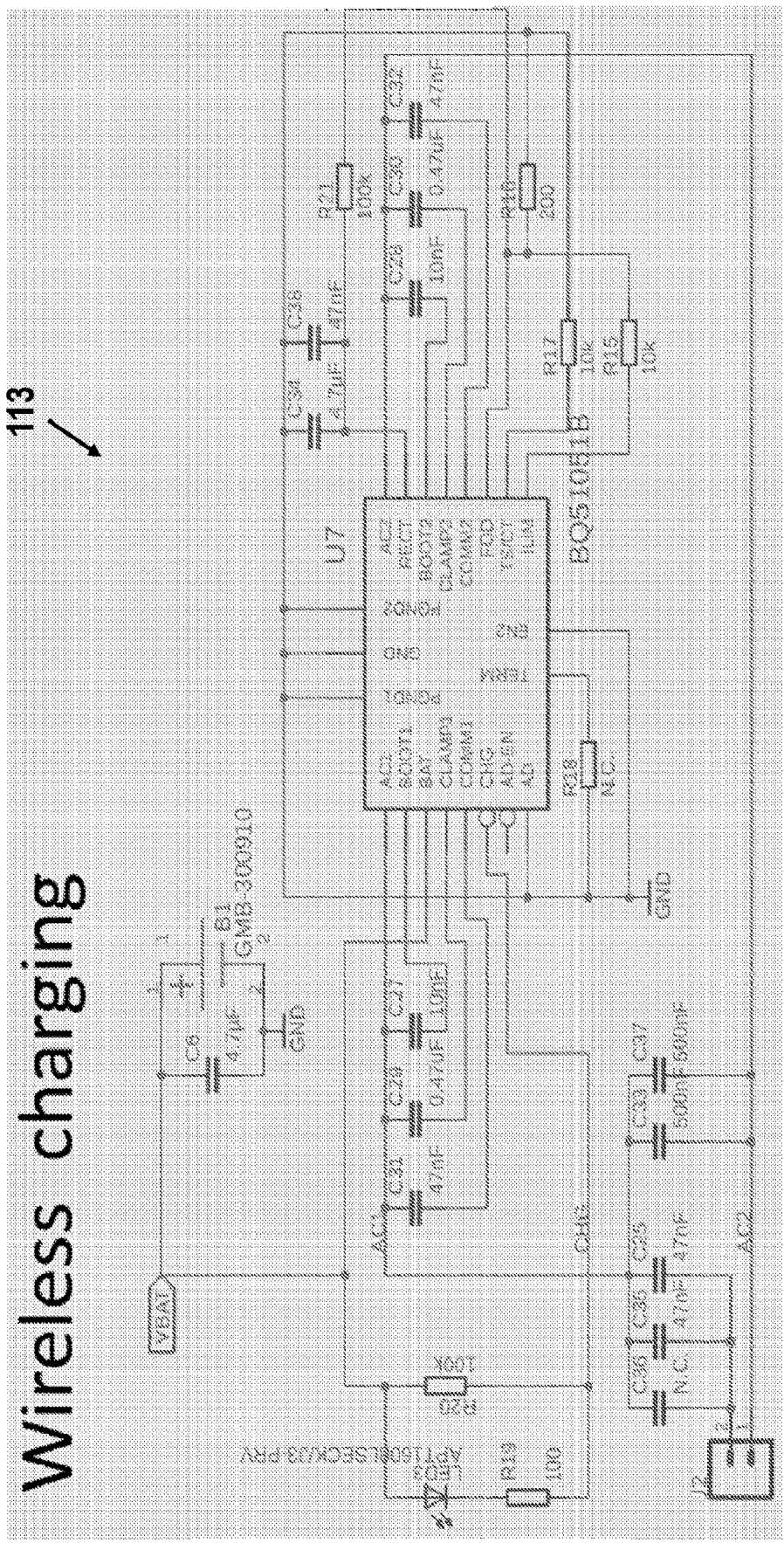
Figure 4D:
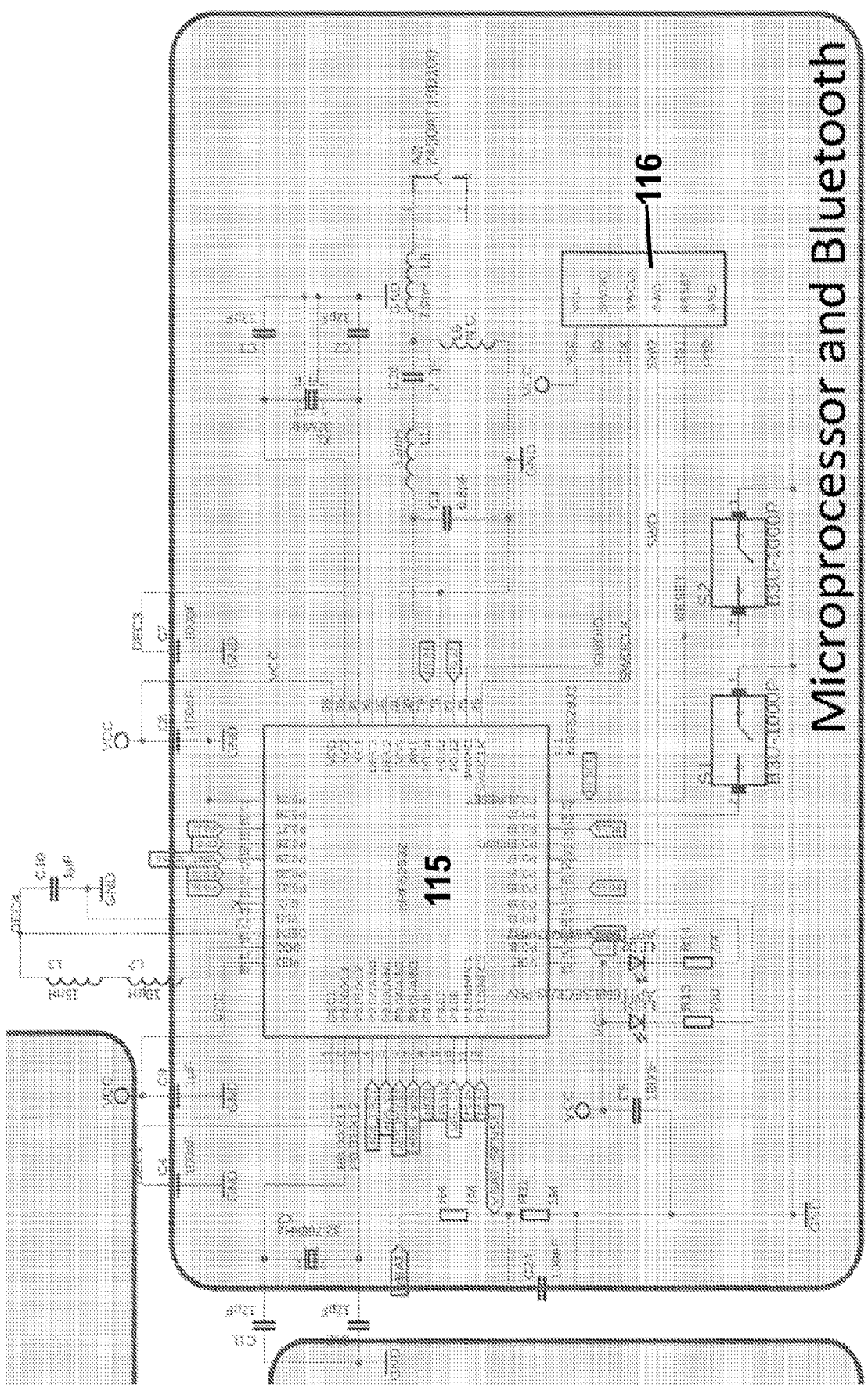
Figure 4E:
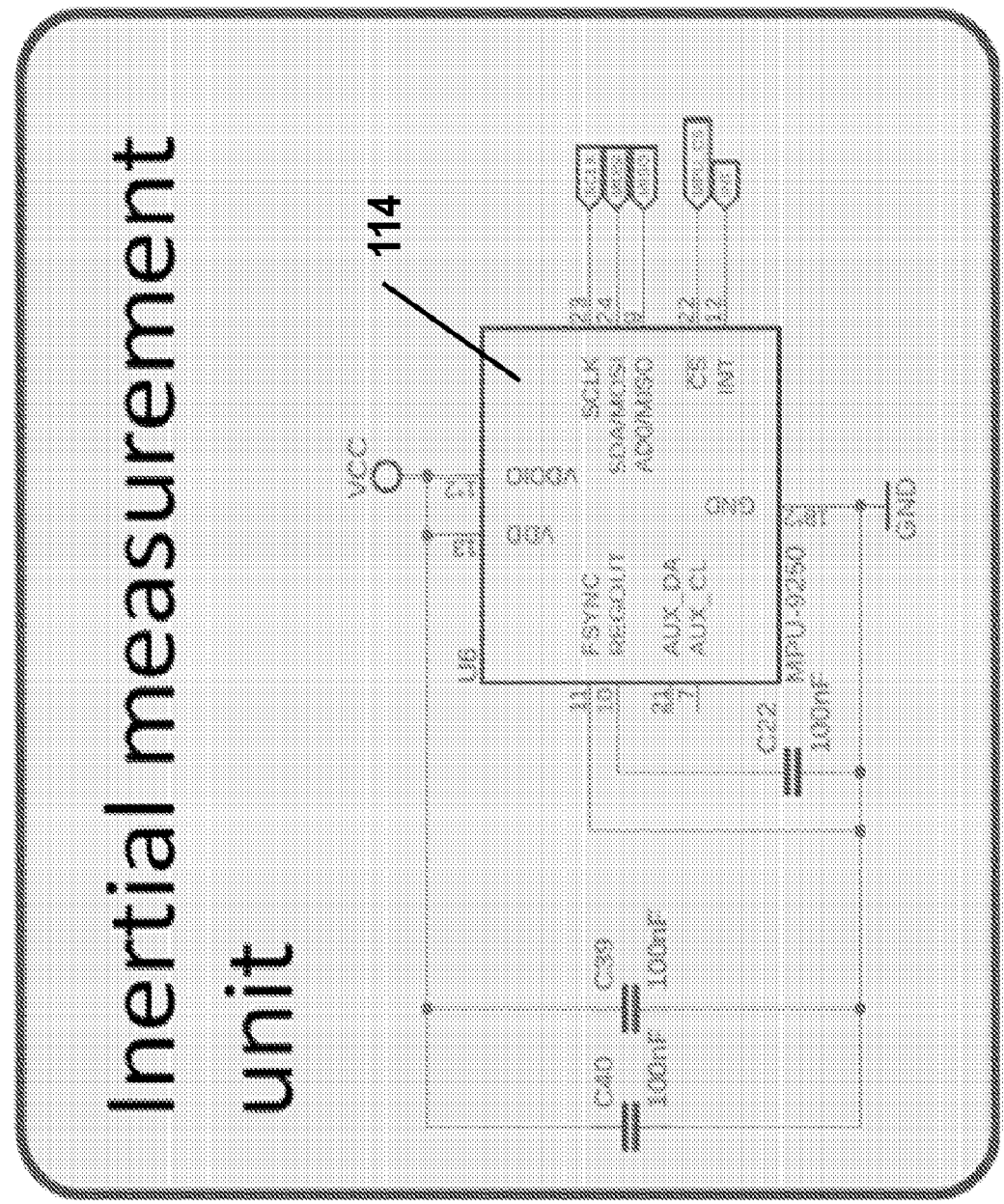

Referring to FIGS. 4-4E, EMG data 182 is acquired using a wireless, wearable EMG sensor 110. The sensor 110 includes an analog-to-digital converter or analog front-end 111 which amplifies and digitizes 8 differential channels at 24 bits and includes integrated patient bias drive circuitry. EMG data 182 are sampled at 500 Hz and acquired by a sensor processor 112 onboard the EMG sensor 110 which then streams the EMG data 182 to the computing device 120 over a wireless connection. As shown in FIGS. 4A-E, the wireless connection is facilitated by a Bluetooth module or antenna 116 in communication with the sensor processor 112. The EMG sensor 110 further includes a charging module 113 which in some embodiments provides Qi-compatible wireless charging. Other components onboard the sensor 110 include an inertial measurement unit 114. The sensor 110 further includes custom firmware installed on the sensor processor 112 which acquires and transmits EMG data 182 to the computing device 120 while minimizing power consumption when not in use. In some embodiments, the firmware timestamps EMG data 182 to allow detection of any dropped samples during transmission. Specific examples of firmware used in FIGS. 4A-4E are shown in Table 1.

TABLE 1

| Sensor Hardware | |
| --- | --- |
| Analog-Digital Converter 111 | ADS1299 (Texas Instruments, Dallas, TX) |
| Sensor Processor 112 | nRF52832 microprocessor (Nordic Semiconductor, Norway) |
| Charging Module 113 | BQ51051B (Texas Instruments, Dallas, TX) |

Software

Referring to FIG. 2, the computing device 120 further includes software 190 stored in a memory 204 and in communication with a processor 202, the software 190 being split into a core service 191 and user applications 192. The core service 191 handles connectivity to the EMG sensors 110 and parses the Bluetooth messages from the EMG sensors 110 into EMG data 182.

The EMG data 182 is passed through the decoder 122 and outputs of the decoder in the form of control signals 188 are made available to the device 120 or other devices or systems depending upon the desired use of the control signals 188. The core service 191 also mirrors data to a cloud server 193 for subsequent analysis and streamed to the machine learning server 130 during optimization. The software 190 was tested on a Pixel 2 and a Samsung Tab S4 and ran without performance issues.

The user applications 192 or other software communicates with the core service 191 to receive updated control signals 188 from the decoder 121. In some embodiments, the following tasks were implemented as user applications:

Optimization Task: During optimization, users were instructed to make self-selected movements to mirror a moving target 161 on the display 160. The target 161 repeatedly cycled along a center-out-center movement and sequentially rotated to move along lines oriented every 45 degrees. An entire cycle moving along these 8 lines took about 30 seconds. This stream of target locations 162 and EMG data 182 is transmitted to the machine learning server 130 and is used to optimize parameters of the decoder 122 as described above. In some embodiments, visual feedback of the output in the form of a cursor 164 (i.e. control signals 188) of the decoder 122 is disabled during calibration as it could bias the user's behavior when the output of an incompletely calibrated decoder 122 does not reach the intended location. The goal during calibration is to collect the natural movements a user 10 would make to indicate a location, which are used during training to map the natural movements of the user to the location. During testing, this calibration routine also worked with a randomly moving target 161, but the predictable center-out rotation was found to be easier and more relaxing to follow.

Figure 5:
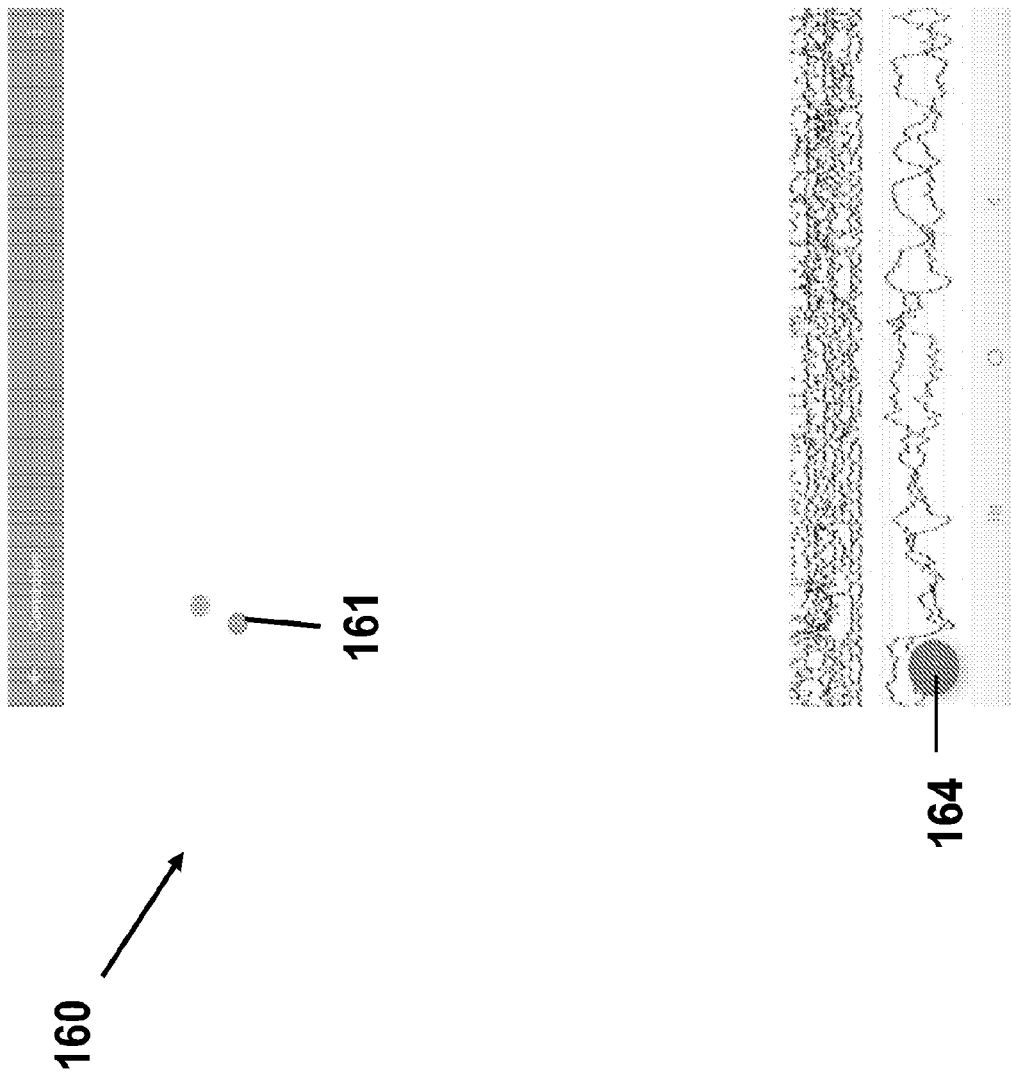
FIG. 5 is a screenshot showing a display of the system of FIG. 1 showing a cursor and a target for training of the system of FIG. 1.

Target Reach Task: A target reaching task was used to assess the performance of the decoder 122. In this task, visual feedback was provided showing the current location of the cursor 164, as shown in FIG. 5. Targets 161 appeared at a random location on the display and the user 10 had ten seconds to reach them. A successful trial was defined as reaching a Euclidean distance less than 10% or 3% of the display size (display coordinates were rescaled from 0 to 1 in both axes, despite the underlying aspect ratio not being 1:1). While during calibration, the user 10 was instructed to make movements to mirror the cursor position, in this task the decoder 121 controlled the cursor velocity.

Figure 6:
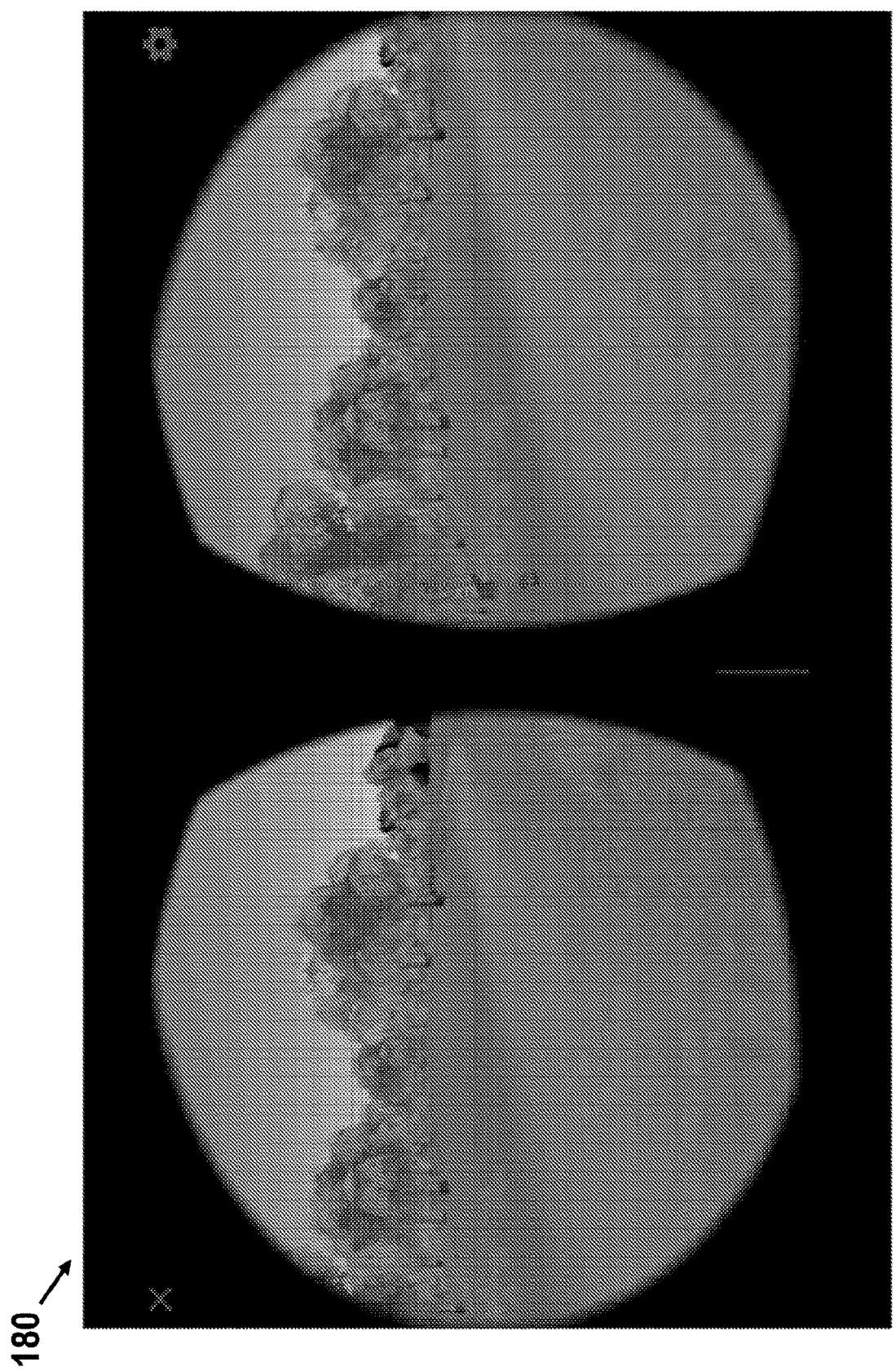
FIG. 6 is a screenshot showing a virtual reality display of one embodiment of the system of FIG. 1.

3) Virtual Reality Navigation: To safely test the feasibility of using the decoder 121 for navigation, a power wheelchair simulation was built that could run on a smart-phone using Unity (Unity Technologies, Denmark). The output of the decoder 122 controlled the wheelchair movement similar to a joystick on a powerchair with forward and backward creating a drive signal and left and right causing the chair to turn. The simulated environment 180, shown in FIG. 6, provided a path through the woods for the user to follow, but had no quantitative goals or scoring. This environment supported Virtual Reality using a Google Daydream headset, or could be viewed directly on the device 110.

EXPERIMENTATION

Experiments were performed at Shirley Ryan AbilityLab, a rehabilitation hospital. All participants provided informed consent and all procedures were approved by Northwestern University's Institutional Review Board. Subject 1 (S1) was a 27 year-old man with non-traumatic incomplete tetraplegia with a C5 lesion recruited during his acute inpatient rehabilitation. Subject 2 (S2) was a 38 year-old man with chronic complete tetraplegia (C4 AIS A) recruited as an outpatient.

Possible movements available to the subject for different directions were discussed at the beginning of each session. Movements were suggested such as "up" corresponding to both shoulders shrugging, "down" as scapular protraction with rhomboid activation, and "left" versus "right" as trying to abduct the corresponding shoulder. Subjects were advised to select movements that were comfortable and intuitive to them and to indicate diagonal directions as a combination of these directions.

Figure 7:
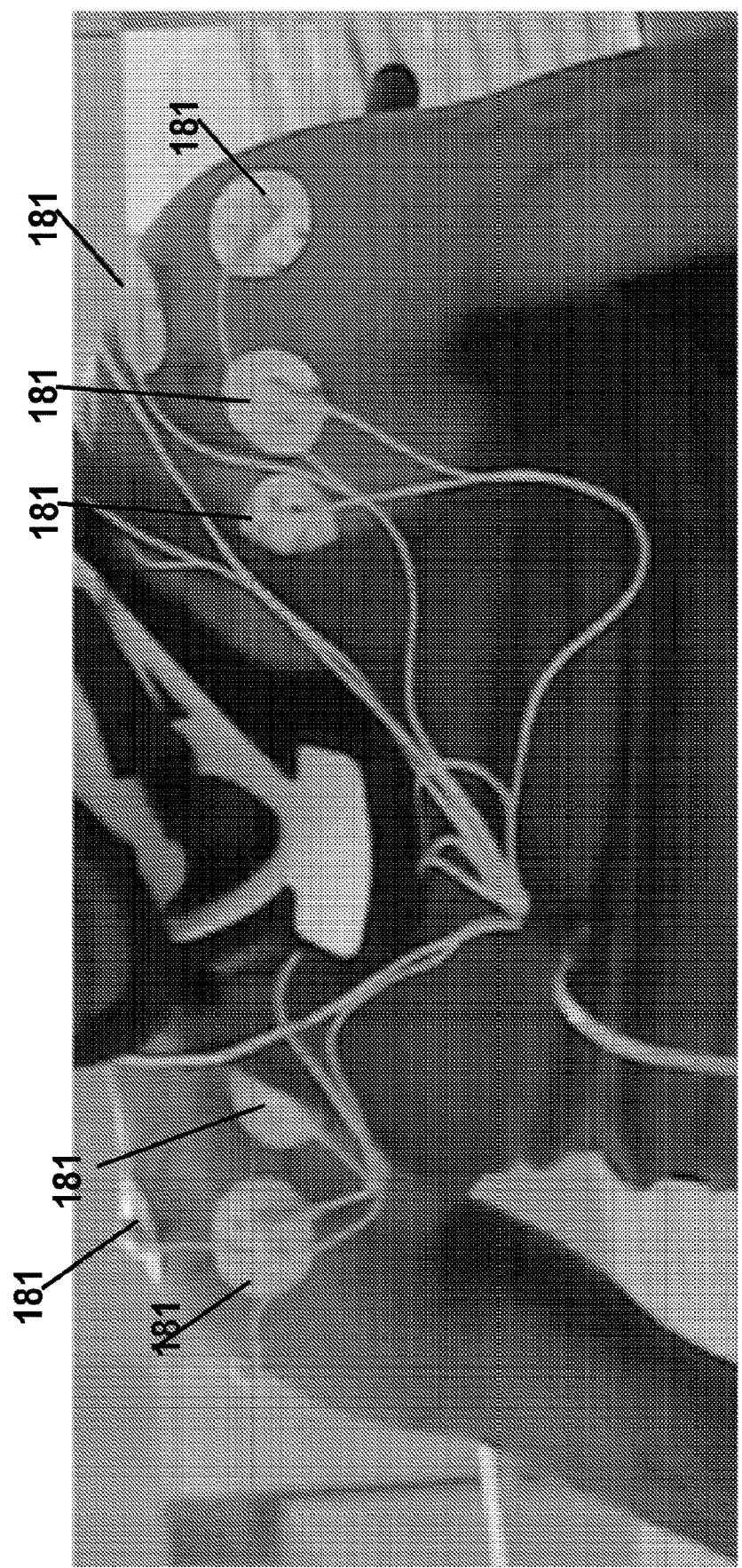
FIG. 7 is a photograph showing a user wearing a plurality of electrodes in communication with the system of FIG. 1.

For both subjects, electrodes 181 were placed over muscles with innervation from upper cervical nerve roots: upper trapezius (C3-C4), rhomboids, (C4-5), deltoid (C5), and the border of anterior deltoid and the clavicular head of pectoralis major (C5-6) with a reference electrode (not shown) placed at the top of the sternum, as shown in FIG. 7. These muscles were selected as they retain some innervation in many people with tetraplegia and impaired hand function and are also less involved in head control. The electrodes 181 were disposable ECG Ag/AgC1 electrodes with a solid hydro-gel adhesive (Bio-Protech Inc, Korea) and were placed as a differential pair from 5 to 10 cm apart on each muscle to be recorded.

Results

Figure 8A:
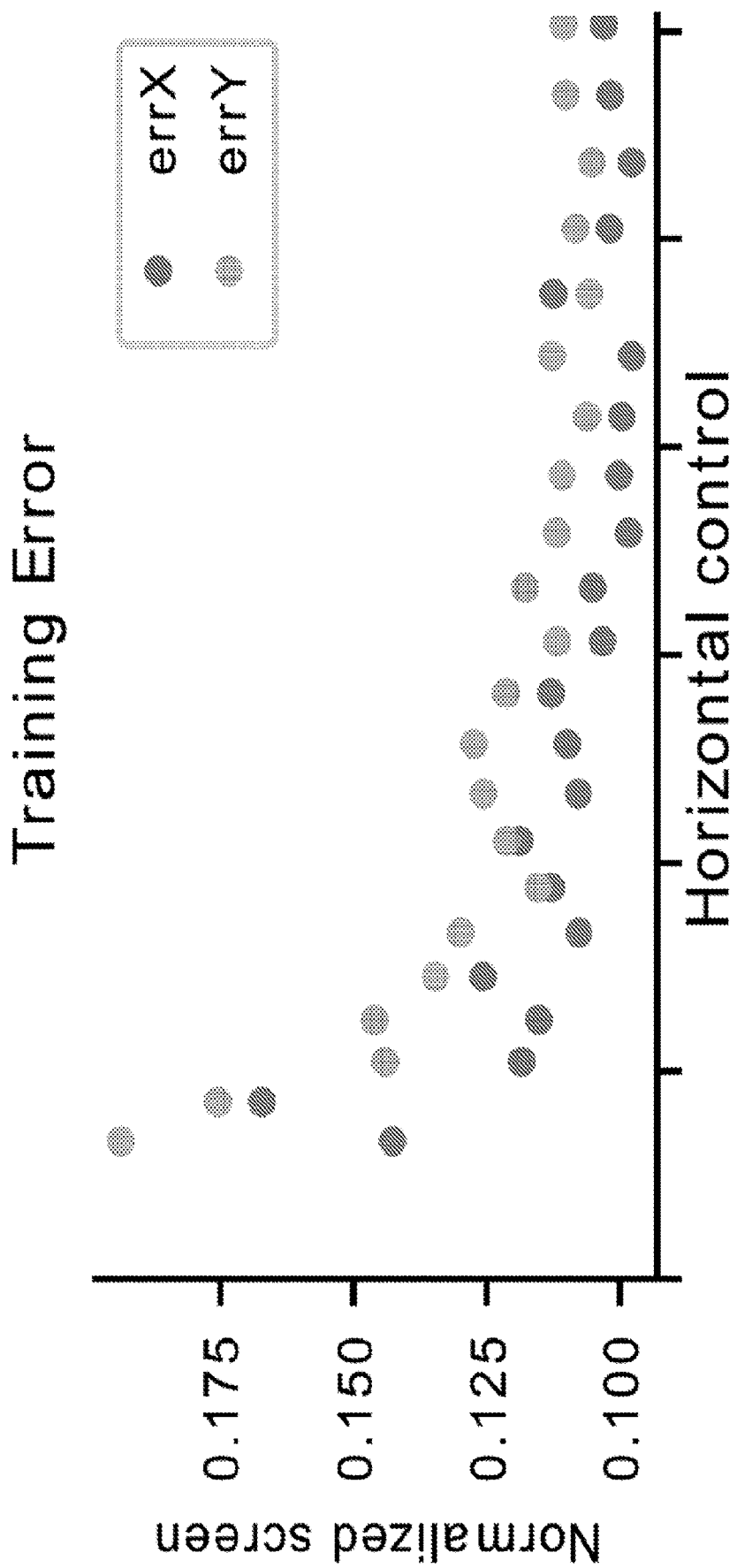
FIGS. 8A-8C are graphical representations showing a calibration session from a test user showing normalized screen space on the vertical axes, FIG. 8A showing error on training data and FIGS. 8B and 8C showing real-time output of the decoder of the system of FIG. 1.
Figure 8B:
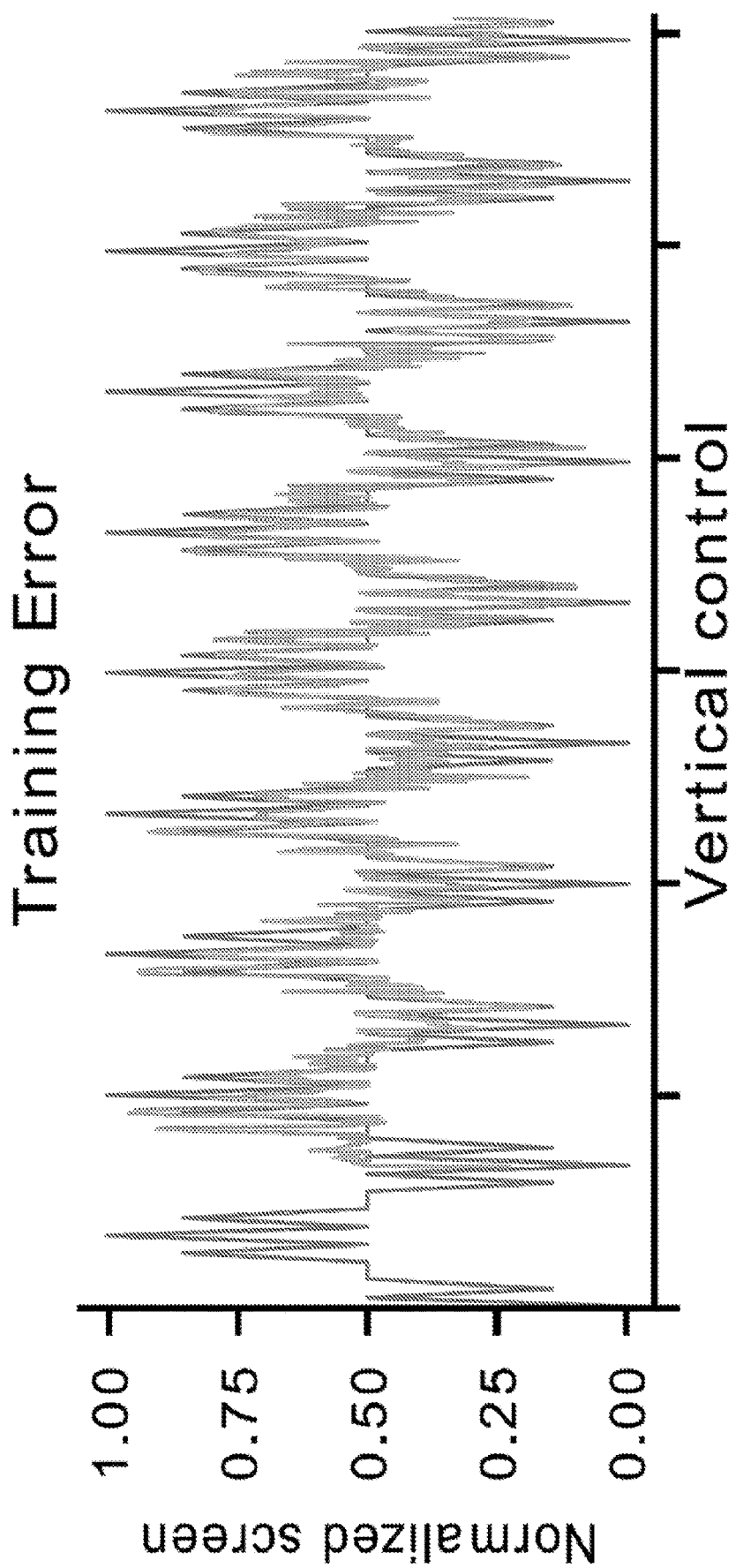
Figure 8C:
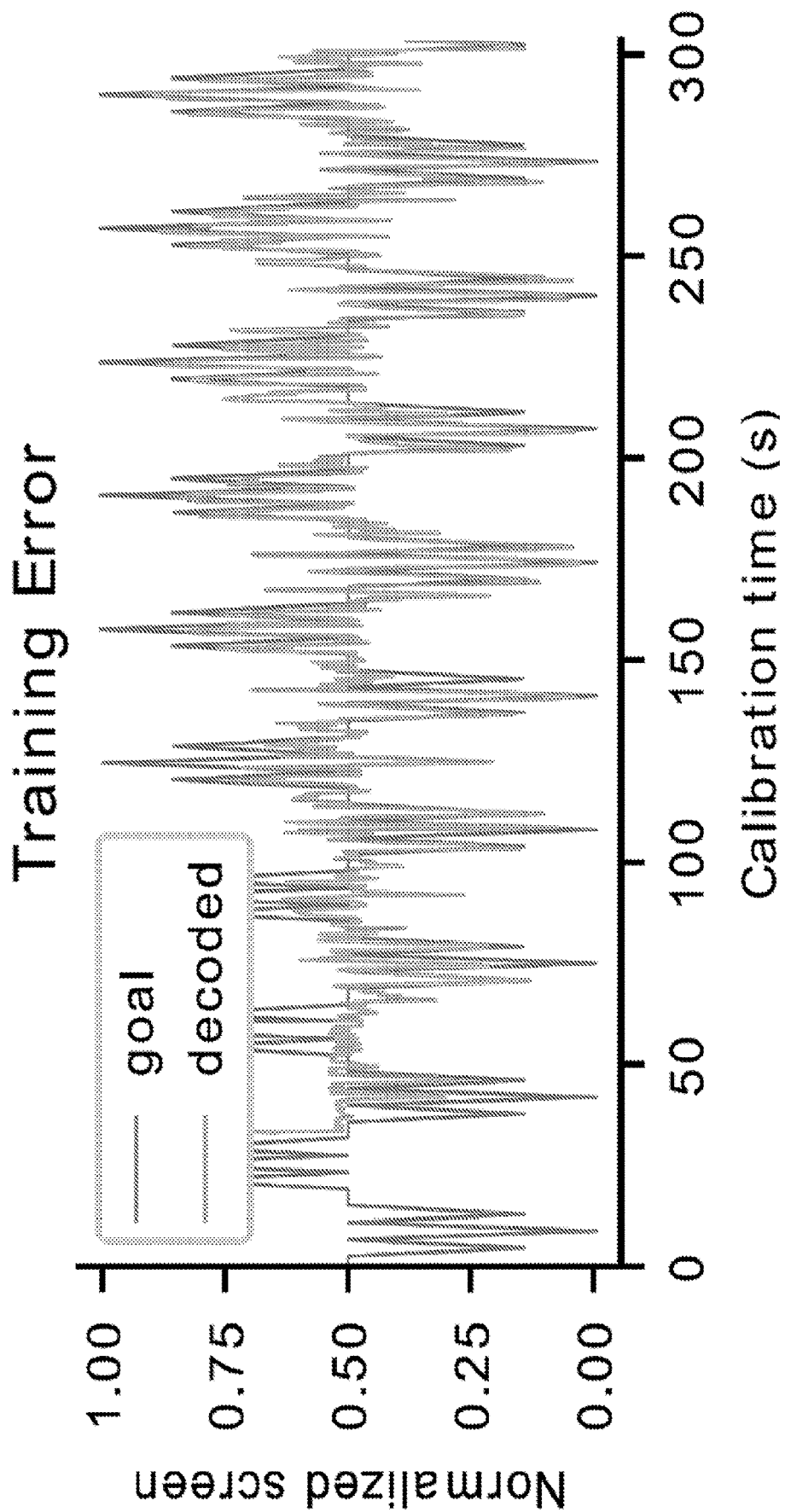

Calibration: The calibration routine had the user 10 follow a moving target 161 by mirroring the target 161 with self-selected movements without visual feedback. Two to three minutes of calibration data were sufficient for the decoder accuracy to saturate with regard to loss function on the training data 163, as shown in FIGS. 8A-8C. No holdout validation data was used during calibration. However, the decoder 122 was running on the computing device 120 while the decoder 122 was being trained by the server 130 (although it was not shown to the subjects) and the outputs demonstrated that after a single iteration through each calibration direction, the real-time performance was fairly good.

Figures 9A, 9B:
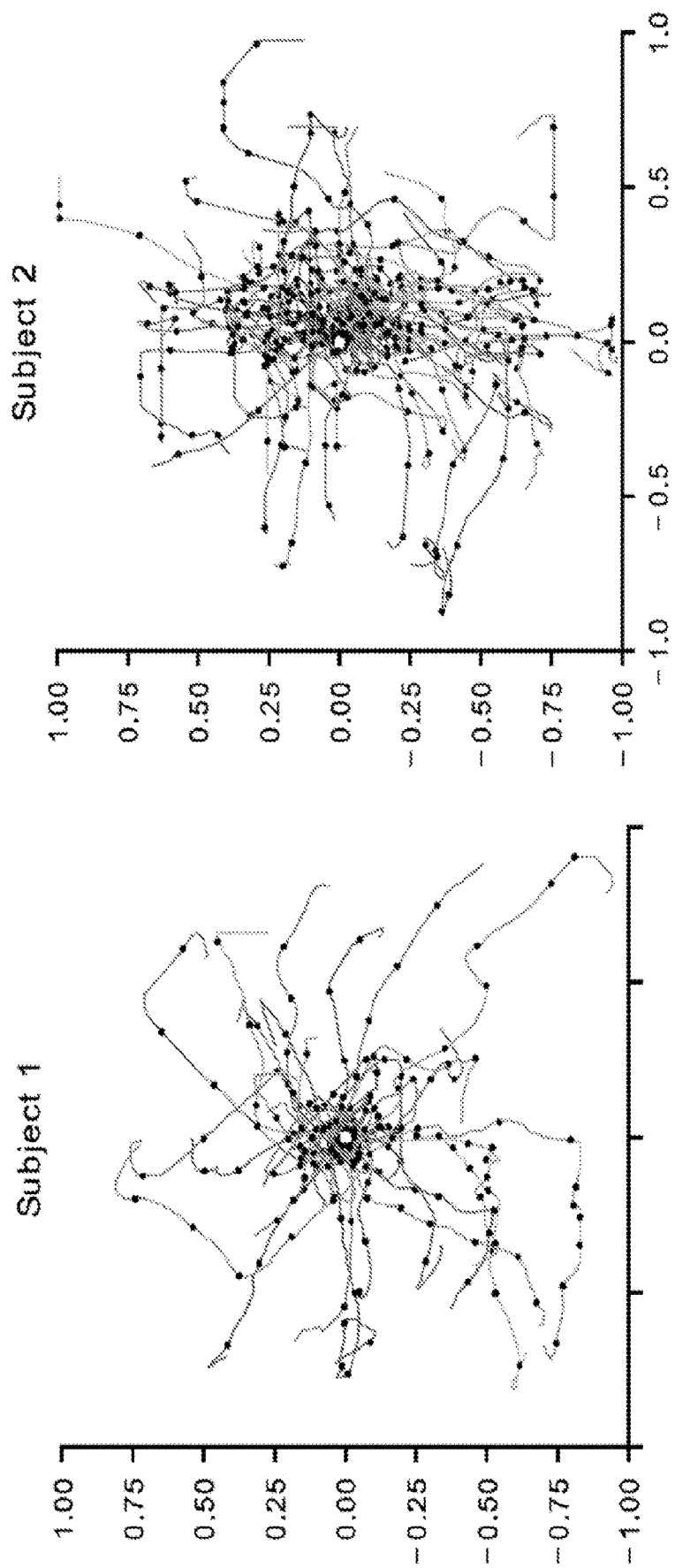
FIGS. 9A and 9B are graphical representations showing target reach task results for both test users for the system of FIG. 1.

Target Reach Task: S1 participated twice in the experiment and S2 participated once. In all three sessions an initial practice run was performed to familiarize them with the tasks. Each session included placement of the electrodes 181 and calibrating the decoder 122. In the target reach task, the participant had 10 seconds to reach the target 161 that appeared randomly on the display 160. On the first session Si was able to hit 52/54 (96%) of the targets 161 with a radius of 0.1 and on the second session was able to his 24/29 (83%) with a target radius of 0.03. S2 had more severe motor impairments and his performance was not quite as good, being only able to hit 28/56 (50%) within the 10 seconds. Trajectories from both subjects are shown in FIGS. 9A and 9B. The trajectories for S2 also show a bias to being on the right of the target 161, and it appeared the subject had a more difficult time sustaining left movement, despite this not being apparent in the calibration data.

Virtual reality navigation: The subjects were both able to control the virtual power wheelchair with the smartphone interface and in virtual reality. This task did not have any navigation objective to allow quantifying performance. Both subjects reported that it was enjoyable (especially the virtual reality) and that they were able to control the powerchair. However, sustained attempts at forward navigation would stop working, which appeared to be due to fatigue and diminishing EMG from the deltoids and trapezoids. This suggests that with the existing controller, directly using the continuous output for prolonged navigation would not work well.

Computing System

Figure 10:
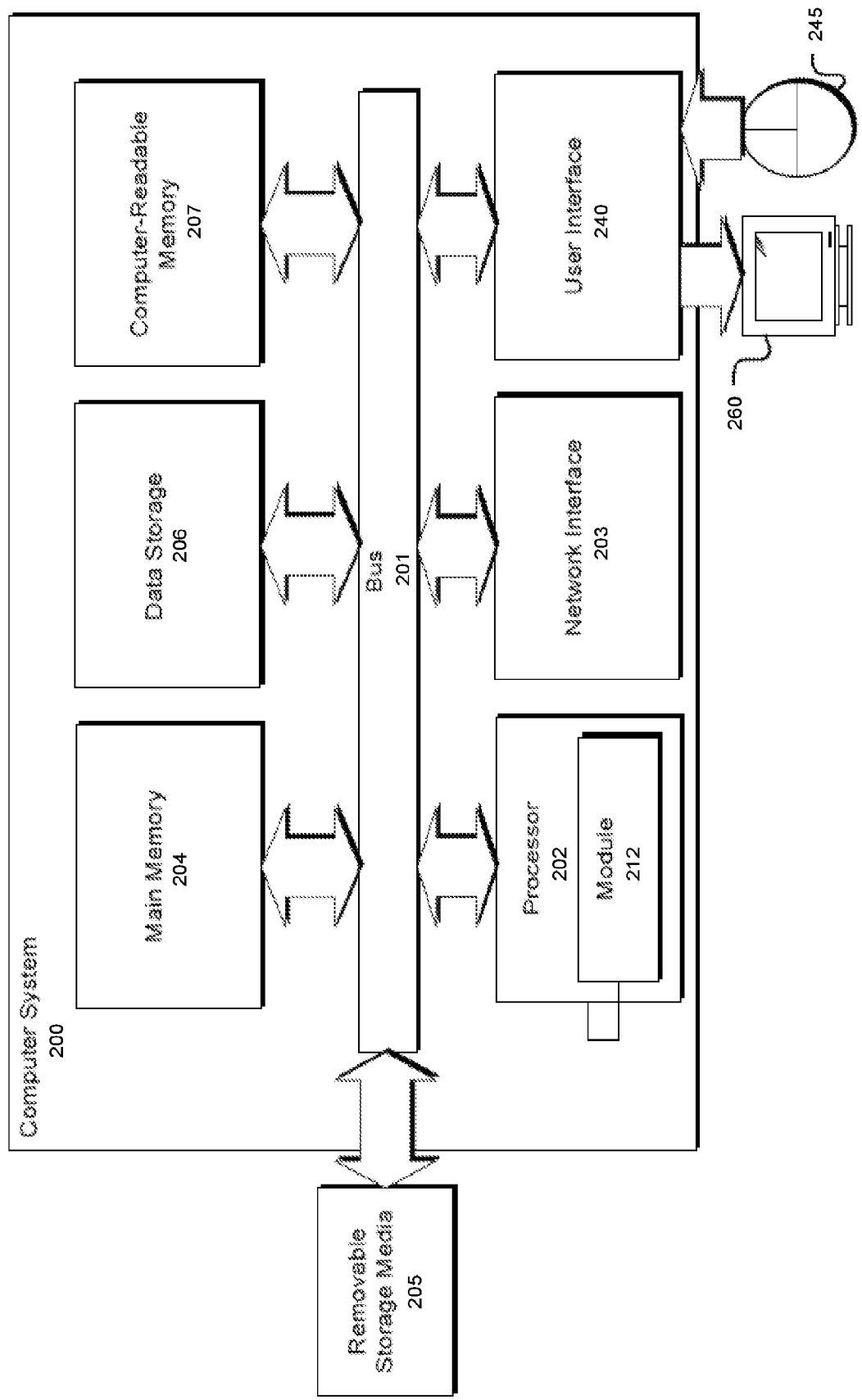
FIG. 10 is a computing system for use with the system of FIG. 1.

FIG. 10 illustrates an example of a suitable computing and networking environment (computer system 200) which may be used to implement various aspects of the present disclosure. In some embodiments, the device to be controlled 101, computing device 120 and/or machine learning server 130 of system 100 are each embodiments of the computer system 200 and may each include additional aspects as described above. Example embodiments described herein may be implemented at least in part in electronic circuitry; in computer hardware executing firmware and/or software instructions; and/or in combinations thereof. Example embodiments also may be implemented using a computer program product (e.g., a computer program tangibly or non-transitorily embodied in a machine-readable medium and including instructions for execution by, or to control the operation of, a data processing apparatus, such as, for example, one or more programmable processors or computers). A computer program may be written in any form of programming language, including compiled or interpreted languages, and may be deployed in any form, including as a stand-alone program or as a subroutine or other unit suitable for use in a computing environment. Also, a computer program can be deployed to be executed on one computer, or to be executed on multiple computers at one site or distributed across multiple sites and interconnected by a communication network.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software, in the form of the system application 190 or otherwise, may include a hardware-implemented module and may accordingly configure a processor 202, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

As illustrated, the computing and networking environment 200 may be a general purpose computing device 200, although it is contemplated that the networking environment 200 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the general purpose computing device 200 may include various hardware components, such as a processing unit 202, a main memory 204 (e.g., a memory or a system memory), and a system bus 201 that couples various system components of the general purpose computing device 200 to the processing unit 202. The system bus 201 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The general purpose computing device 200 may further include a variety of computer-readable media 207 that includes removable/non-removable media and volatile/nonvolatile media, but excludes transitory propagated signals. Computer-readable media 207 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EPSOM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the general purpose computing device 200. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 204 includes computer storage media in the form of volatile/nonvolatile memory such as read only memory (ROM) and random access memory (RAM). A basic input/output system (BIOS), containing the basic routines that help to transfer information between elements within the general purpose computing device 200 (e.g., during start-up) is typically stored in ROM. RAM typically contains data and/or program modules that are immediately accessible to and/or presently being operated on by processing unit 202. For example, in one embodiment, data storage 206 holds an operating system, application programs, and other program modules and program data.

Data storage 206 may also include other removable/non-removable, volatile/nonvolatile computer storage media. For example, data storage 206 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules and other data for the general purpose computing device 200.

A user may enter commands and information through a user interface 240 or other input devices 245 such as a tablet, electronic digitizer, a microphone, keyboard, and/or pointing device, commonly referred to as mouse, trackball, or touch pad. Other input devices 245 may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices 245 are often connected to the processing unit 202 through a user interface 240 that is coupled to the system bus 201, but may be connected by other interface and bus structures, such as a parallel port, game port or a universal serial bus (USB). A monitor 260 or other type of display device is also connected to the system bus 201 via user interface 240, such as a video interface. The monitor 260 may also be integrated with a touch-screen panel or the like.

The general purpose computing device 200 may operate in a networked or cloud-computing environment using logical connections of a network Interface 203 to one or more remote devices, such as a remote computer. The remote computer may be a personal computer, a server, a router, a network PC, a peer device or other common network node, and typically includes many or all of the elements described above relative to the general purpose computing device 200. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the general purpose computing device 200 may be connected to a public and/or private network through the network interface 203. In such embodiments, a modem or other means for establishing communications over the network is connected to the system bus 201 via the network interface 203 or other appropriate mechanism. A wireless networking component including an interface and antenna may be coupled through a suitable device such as an access point or peer computer to a network. In a networked environment, program modules depicted relative to the general purpose computing device 200, or portions thereof, may be stored in the remote memory storage device.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for electromyography (EMG)-based control using neural networks, comprising:
   one or more wearable sensors that generate EMG data; and
   a computing device implementing a decoder including a neural network trained to decode EMG data generated in response to muscle activity of a user to one or more control signals configured to continuously control a predetermined device;
   wherein the neural network is trained using a training set comprising a target location of each of a plurality of calibration targets and training EMG data generated in response to the user performing one or more self-selected movements indicative of movement to the target location of each of the plurality of calibration targets.

2. The system of claim 1, wherein the decoder is optimized based on trained policy such that the decoder and a behavioral policy are jointly optimized together.

3. The system of claim 1, wherein the decoder is trained using supervised learning with backpropagation to train a function to map the training EMG data to the target location of each of the plurality of calibration targets, wherein the function includes parameters of the decoder.

4. The system of claim 3, wherein the parameters of the decoder are optimized using a loss function, wherein the loss function minimizes a difference between the target location and a corresponding control signal sample of the one or more 2D continuous control signals for each of a plurality of EMG samples.

5. The system of claim 1, wherein the neural network further comprises:
   a plurality of fixed neural network layers defined by the decoder and configured for determining a root-mean power in EMG bandwidth of the EMG data for each channel of a plurality of channels.

6. The system of claim 5, wherein the neural network further comprises:
   a convolutional layer in communication with the plurality of fixed neural networks and configured to obtain a plurality of features associated with the EMG data within a predetermined time interval for each of the plurality of channels; and
   a plurality of densely-connected layers in communication with the convolutional layer and configured to obtain the one or more control signals using each of the plurality of features.

7. The system of claim 1, wherein the training data set is sampled in a biased manner such that newer training data is considered with greater weight than older training data.

8. The system of claim 1, wherein the decoder as trained is implemented by the device to control one of a velocity of a cursor on a display and a power wheelchair in virtual reality.

9. The system of claim 1, wherein the decoder is continually refined by applying deep reinforcement learning with a behavioral policy.

10. The system of claim 1, wherein the one or more 2D continuous control signals include one of a two-dimensional continuous cursor and a two-dimensional cursor with binary signals.

11. The system of claim 1, wherein the decoder implemented by the computing device maps multichannel activity defined by the EMG data into the 2D continuous control signals.

12. The system of claim 1, wherein the computing device includes a smartphone, laptop, or tablet.

13. A method of electromyography (EMG)-based control using neural networks, comprising:
   providing a system comprising:
      one or more wearable sensors that generate EMG data; and
      a computing device implementing a decoder including a neural network;
   generating, with the system, a training data set comprising a target location of each of a plurality of calibration targets and training EMG data generated in response to the user performing one or more self-selected movements indicative of movement to the target location of each of the plurality of calibration targets; and
   training the neural network based on the training data to decode EMG data generated in response to muscle activity of a user to one or more 2D continuous control signals configured to continuously control a predetermined device;
   transmitting a trained decoder to the computing device; and
   continuously controlling the predetermined device based on the one or more 2D continuous control signals decoded by the trained decoder.

14. The method of claim 13, wherein the step of mapping the EMG data to the one or more control signals further comprises:
   determining a root-mean power in EMG bandwidth for each channel of the plurality of channels using a set of fixed neural network layers of the decoder;
   obtaining a plurality of features using a convolutional layer of the decoder, the convolutional layer configured to capture spatio-temporal patterns associated with EMG data within a predetermined time interval for each of the plurality of channels; and obtaining one or more control signals using a plurality of densely-connected layers of the decoder and each of the plurality of features.

15. The method of claim 13, wherein newer training data is sampled with a greater weight than older training data.

* * * * *